United States Patent
Daily et al.

(10) Patent No.: US 10,295,491 B2
(45) Date of Patent: May 21, 2019

(54) MINERAL INSULATED SHEATHED ASSEMBLY WITH INSULATION RESISTANCE INDICATOR

(71) Applicants: Jeffrey N. Daily, Houston, TX (US); Raymond B. Litteaur, Houston, TX (US)

(72) Inventors: Jeffrey N. Daily, Houston, TX (US); Raymond B. Litteaur, Houston, TX (US)

(73) Assignee: Daily Instruments, Houston, TX (US)

( * ) Notice: Subject to any disclaimer, the term of this patent is extended or adjusted under 35 U.S.C. 154(b) by 395 days.

(21) Appl. No.: 15/152,398

(22) Filed: May 11, 2016

(65) Prior Publication Data

US 2017/0328852 A1  Nov. 16, 2017

(51) Int. Cl.
| | | |
|---|---|---|
| *G01K 7/00* | (2006.01) | |
| *G01K 1/00* | (2006.01) | |
| *G01N 27/20* | (2006.01) | |
| *G01R 31/12* | (2006.01) | |
| *G01K 1/08* | (2006.01) | |
| *G01K 15/00* | (2006.01) | |
| *G01K 7/06* | (2006.01) | |

(52) U.S. Cl.
CPC ............ *G01N 27/205* (2013.01); *G01K 1/08* (2013.01); *G01K 7/06* (2013.01); *G01K 15/007* (2013.01); *G01R 31/12* (2013.01)

(58) Field of Classification Search
USPC ........................................ 374/179, 208, 166
See application file for complete search history.

(56) References Cited

U.S. PATENT DOCUMENTS

| | | | | |
|---|---|---|---|---|
| 3,923,552 | A * | 12/1975 | Parris ....................... | G01K 1/08 136/227 |
| 4,183,248 | A | 1/1980 | West | |
| 5,158,366 | A * | 10/1992 | Nagai ................. | F27D 21/0014 338/28 |
| 6,536,950 | B1 * | 3/2003 | Green ..................... | G01K 1/10 374/141 |
| 8,911,148 | B2 * | 12/2014 | Martensson ............. | G01K 1/08 338/226 |
| 2007/0258506 | A1 | 11/2007 | Schwagerman et al. | |
| 2011/0224907 | A1 * | 9/2011 | Chalifoux ............... | E21B 47/06 702/11 |
| 2013/0070808 | A1 | 3/2013 | Daily et al. | |

(Continued)

FOREIGN PATENT DOCUMENTS

JP  10-325759 A  12/1998

OTHER PUBLICATIONS

International Search Report issued in connection with corresponding International patent application No. PCT/US2017/046492, dated Nov. 22, 2017, 3 pages.

*Primary Examiner* — Mirellys Jagan
(74) *Attorney, Agent, or Firm* — Duane Morris LLP; Diana M. Sangalli

(57) ABSTRACT

An assembly includes an electrical conductor disposed within an elongate mineral insulated conductive sheath. The electrical conductor is electrically grounded to the conductive sheath. The assembly also includes a test conductor disposed within and electrically isolated from the sheath to provide an indication of the insulation resistance of the assembly.

6 Claims, 2 Drawing Sheets

(56) References Cited

U.S. PATENT DOCUMENTS

2013/0243035 A1\* 9/2013 Walling ................ G01K 7/021
  374/179
2016/0178448 A1 6/2016 Mella
2016/0252404 A1\* 9/2016 Terada .................... G01K 1/08
  374/179

\* cited by examiner

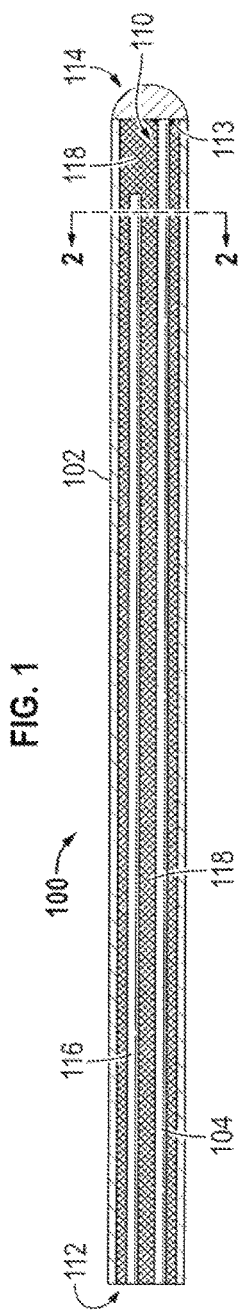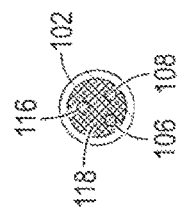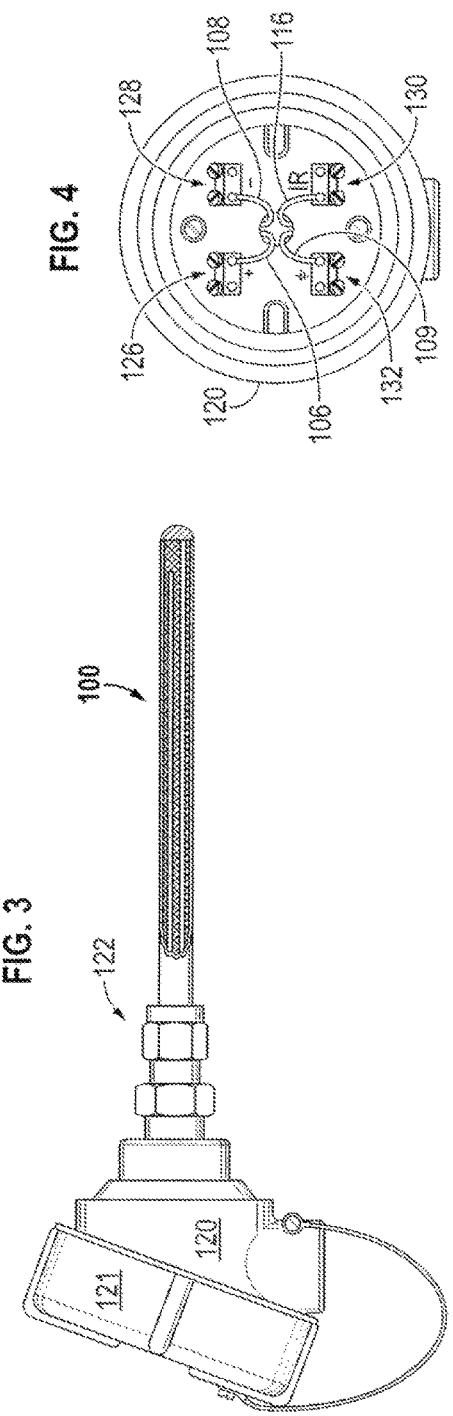

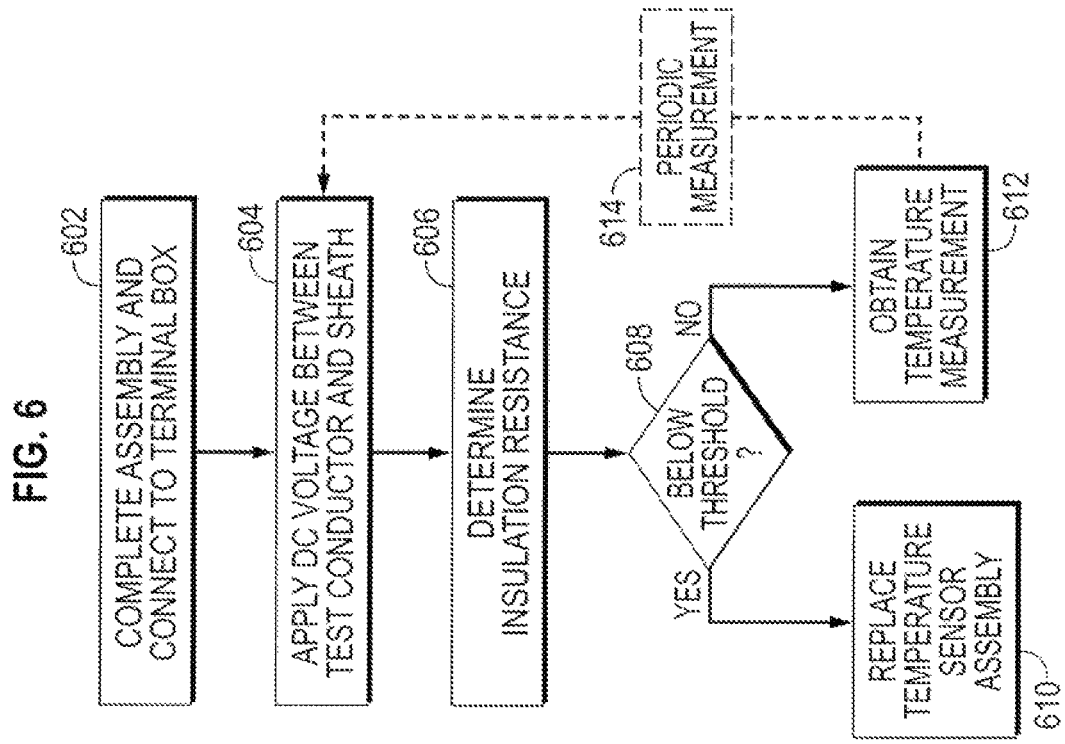
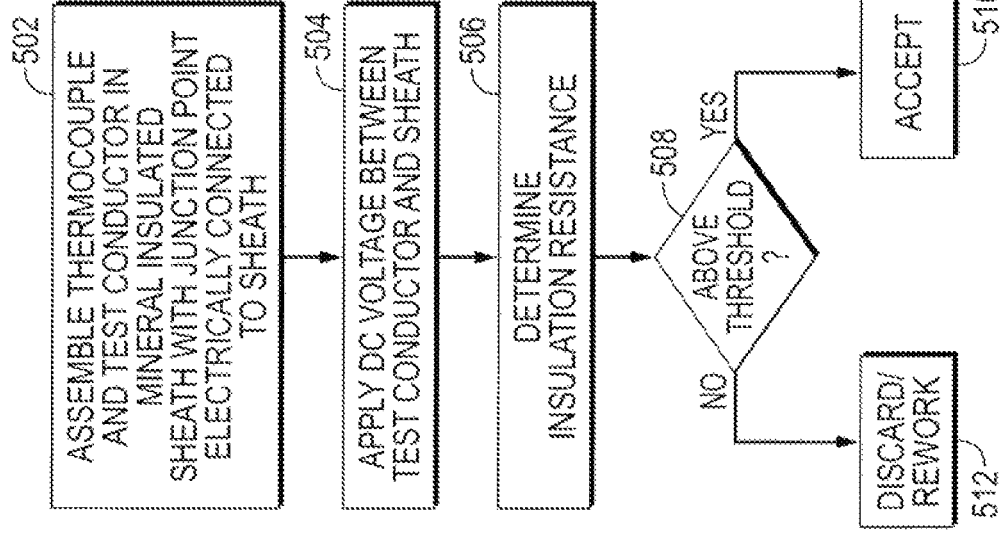

MINERAL INSULATED SHEATHED ASSEMBLY WITH INSULATION RESISTANCE INDICATOR

TECHNICAL FIELD

The present invention relates generally to mineral insulated sheathed assemblies, such as temperature sensing assemblies and heating element assemblies, and, more particularly, to a mineral insulated sheathed assembly having a conductive element and an insulation resistance indicator contained within a conductive sheath.

BACKGROUND

A variety of temperature sensors can be used in environments that require the temperature sensor to be contained within a protective sheath. For example, the temperature sensors can be used in applications, such as high temperature and/or high pressure processes, that require that the sensor be protected to some degree from the extreme environment. In some applications, the protective sheath is made of a conductive material that is electrically grounded in the setup in which the temperature sensor is deployed. In many setups, the temperature sensor is configured as a thermocouple with a junction point that also is electrically grounded. For example, the thermocouple can be electrically grounded by electrically coupling the thermocouple to the conductive sheath. The sheath is filled with an electrically insulative material to isolate the conductors making up the thermocouple from each other and from the inner wall of the sheath (except for the junction point). Because the junction point is grounded to the sheath, a measure of the insulation resistance of the temperature sensor (i.e., a measure of the integrity of the electrically insulative material isolating the conductors from each other and from the inner wall of the sheath) cannot be made. Accordingly, an imminent failure of the temperature sensor may go undetected until the sensor actually fails. Inaccuracies in temperature measurements also may go undetected.

Assemblies also are used that include heating elements contained within a mineral insulated conductive sheath. In such assemblies, current is applied to a conductive element within the sheath to generate heat. The sheath may then be positioned adjacent or wrapped around another structure to keep that structure warm. These assemblies also can fail if the integrity of the insulative material in the sheath is compromised.

BRIEF DESCRIPTION OF THE DRAWINGS

Certain embodiments of the invention will hereafter be described with reference to the accompanying drawings, wherein like reference numerals denote like elements. It should be understood, however, that the accompanying drawings illustrate only the various implementations described herein and are not meant to limit the scope of various technologies described herein. The drawings are as follows:

FIG. 1 is a schematic representation of a cross-section of a temperature sensing assembly according to an embodiment.

FIG. 2 is a cross-section taken along the line 2-2 of FIG. 1.

FIG. 3 illustrates the temperature sensing assembly of FIG. 1 connected to an exemplary terminal box according to an embodiment.

FIG. 4 is a schematic representation of a face of the terminal box showing the connection terminals according to an embodiment.

FIG. 5 is a diagram illustrating an exemplary procedure for assembling and testing insulation resistance of a temperature sensing device according to an embodiment.

FIG. 6 is a diagram illustrating an exemplary procedure for deploying a temperature sensing device and testing insulation resistance during use according to an embodiment.

DETAILED DESCRIPTION

Embodiments of the invention provide a temperature sensing assembly disposed within a conductive sheath. The temperature sensing assembly includes a thermocouple with a grounded junction point and an electrically insulative material surrounding the conductors disposed within the sheath that make up the thermocouple. The assembly further includes an electrical conductor contained within the sheath and arranged to provide an indication of the insulation resistance of the assembly, as will be described in further detail below.

An example of a sheathed temperature sensing assembly 100 according to one embodiment is shown schematically in the cross-section view of FIG. 1. The assembly 100 includes a sheath 102 made of a conductive material (e.g., stainless steel, Inconel, nickel alloy) and a thermocouple 104 made of a pair of electrical conductors 106, 108 of dissimilar materials, such as iron/constantin, chromel/alumel, copper/constantan, joined at a temperature sensing junction 110. The sheath 102 comprises an open interior into which the pair of electrical conductors 106, 108 extend through an open end 112 to a distal end 114. In the embodiment of FIG. 1, the electrical conductors 106, 108 extend along the length of the sheath 102 and are joined to form the sensing junction 110 at the distal end 114 of the sheath 102. The junction 110 is electrically connected to the sheath 102, such as by a weld 113, so that, in use, both the junction 110 and the sheath 102 are at the same electrical potential. Generally, in use, the junction 110 and the sheath 102 are electrically grounded.

Although FIG. 1 shows the junction 110 at the distal end 114 of the sheath 102, it should be understood that the junction 110 may be located at any desired position along the length of the sheath 102. Further, although only one conductor pair 106, 108 is shown, more than one conductor pair can be included within the sheath 102. The assembly of FIG. 1 also includes a third electrical conductor 116, referred to as a test conductor, extending into the open interior of the sheath 102 through the open end 112 approximately to the distal end 114.

An insulation material 118, such as an electrical insulation material, is disposed about the individual conductors 106, 108, 116 contained within the sheath 102. The insulation material 118 generally fills the interior about each of the conductors 106, 108 of the conductor pair and the test conductor 116. Although various electrical insulation materials may be used, exemplary materials are magnesium oxide (MgO) and alumina oxide. The insulation material 118 electrically isolates each of the conductors 106, 108, 116 from the others and from the inside wall of the sheath 102 except at the junction point 110. Maintaining the electrical isolation between conductors 106, 108, 116 and the sheath 102 (except at the junction point 110) helps ensure that the temperature measurement provided by the junction point 110 is accurate, reliable and will not drift.

FIG. 2 shows a cross section of the temperature sensing assembly 100 taken generally along the line 2-2 of FIG. 1, showing the conductor pair 106, 108 and the test conductor 116 disposed within the interior space 112 of the sheath 102. The conductor pair 106, 108 and the test conductor 116 are surrounded by the insulative material 118.

In the embodiments shown, an insulation resistance test to measure the integrity of the insulation material 118 is performed, such as in accordance with the requirements of ASTM E585 and E780. In general, an insulation resistance on the order of 1 Gohm at 500 VDC at ambient temperature is acceptable to ensure the integrity of the temperature measurement provided by the junction point 110. Lower insulation resistances (e.g., in the tens of Kohm range) can indicate the presence of moisture within the interior space 112 of the sheath 102, which not only will affect the measurement, but can lead to corrosion of the conductors 106, 108 and ultimately failure of the temperature sensing assembly 100. Thus, the ability to measure insulation resistance at the time of manufacture and during use can provide useful information. Generally, the insulation resistance would be measured by applying an electrical potential between the conductor pair 106, 108 and the sheath 102. However, for temperature sensing assemblies having the junction 110 electrically connected to the sheath 102, a measurement of insulation resistance cannot be made. Thus, in the embodiment shown in FIG. 1, the third conductor 116 (i.e., the test conductor) is provided to measure the insulation resistance of the temperature sensing assembly 100.

When deployed in the application in which the temperature measurements are made, the conductors 106, 108, 116 within the sheath 102 are connected to a terminal box 120 or other suitable arrangement that provides ready access to apply and/or measure electrical signals present on the conductors 106, 108, 116. As shown in FIG. 3, an exemplary terminal box 120 with an access cover 121 can be coupled to the sheath 102 through an appropriate mechanical coupling 122 and each of the conductors 106, 108, 116 extends from the open end 112 of the sheath 102 and is connected to terminals 126, 128, 130 that are accessible to an operator of the temperature sensing assembly 100. The face of an exemplary terminal box 120 is shown schematically in FIG. 4, which includes the pair of terminals 126, 128 electrically connected to the conductor pair 106, 108 of the thermocouple, a third terminal 132 that is electrically grounded, and a fourth terminal 130 that is electrically connected to the test conductor 116. The terminal 132 is electrically grounded via a conductor 109 that can be directly connected to sheath 102 or can be electrically connected to the sheath 102, such as by a connection to an electrically conductive transition housing. The insulation resistance measurement can be made by applying a DC voltage across the fourth and third terminals 130, 132.

The measurement can be made at various points during the manufacturing/assembly process and before the temperature sensing assembly 100 is deployed to the field. The measurement also can be made periodically during use of the temperature sensing assembly 100 in the field to check the integrity of the temperature measurements and/or to determine or predict whether a failure has or will occur.

For example, as shown in the flow diagram in FIG. 5, the thermocouple 104 and test conductor 116 can be assembled in a mineral insulated sheath 102 with the junction point 110 welded to the sheath 102 at the desired temperature sensing location and the sheath 102 can be compacted (block 502). A DC voltage (e.g., 500 VDC or other value appropriate for the particular assembly 100) can then be applied between the test conductor 116 (block 504), and the sheath 102 and the insulation resistance determined from an electrical measurement made between the conductor 116 and sheath 102 (block 506). For example, the insulation resistance can be determined by measuring the electrical current flowing between test conductor 116 and the sheath 102 using appropriate instrumentation. If the determined insulation resistance is above a predetermined threshold (e.g., 10 Gohms or other value appropriate for the particular assembly 100) (block 508), then the integrity of the assembly 100 can be deemed adequate and the assembly 100 can be accepted for further processing and/or deployment for use (block 510). Otherwise, the assembly 100 can be rejected and discarded or reworked (block 512).

If the temperature assembly 100 is accepted, then further assembly steps and/or deployment in the field can be performed. For example, as shown in the flow diagram of FIG. 6, an accepted temperature sensing assembly 100 can be connected to a terminal box, such as the exemplary terminal box 120, via appropriate mechanical couplings and electrical connections (block 602). At this point, the insulation resistance can again be tested (or might be tested for the first time) by applying a DC voltage (e.g., 500 VDC or other appropriate value) between the test conductor 116 and the sheath 102 (block 604). As an example, the voltage can be applied across the appropriate terminals of the terminal box 120. The insulation resistance of the assembly 100 can then be determined based on measurement of an electrical parameter (e.g., current) between the terminals of the terminal box 120 (block 606). If the determined insulation resistance is below a threshold amount (e.g., 1 Gohm) (block 608), then, if the assembly 100 has been deployed in the field, it should be replaced (block 610). Otherwise, the assembly 100 can be used or continue to be used to monitor temperature in the field deployment (block 612). While in the field, periodic measurements to determine insulation resistance can be made (block 614) to ensure the continued integrity of the assembly 100 and the temperature measurements obtained therefrom. If at some point during the life of the assembly 100 the determined insulation resistance falls below an acceptable threshold, then the assembly 100 can be replaced (block 610) before it fails altogether.

Various processes may be used to form the temperature sensing assembly 100. One exemplary methodology comprises extending the conductors 106, 108, 116 into the interior of the sheath 102, welding the dissimilar conducting materials 106, 108 together at a junction point 110, and welding the junction point 110 to the sheath 102 at a desired location. The insulation 118 can initially be placed within the sheath 102 in the form of beads. The sheath 102 and insulation 118 can then be compacted (e.g., by drawing, swaging, etc.) 102 so that the insulation 118 fills the interstices between conductors 106, 108, 116. At this point in the assembly, the insulation resistance can be measured by applying a DC voltage (e.g., 500 VDC) between the sheath 102 and the test conductor 116 as discussed above. The conductors 106, 108, 116 of the temperature sensing assembly 100 can then be electrically coupled to appropriate terminals in the terminal box 120 and used to monitor temperature in the field.

In other embodiments of the invention, the assembly 100 can be a heater cable and one or more of the conductors 106, 108 may be configured as heating elements, where the length and the resistance of conductors 106 and/or 108 are selected to provide a desired Watts per foot for the particular application in which the heater cable is employed. Insulation resistance of the heater cable assembly then can be measured using the test conductor 116 in the manner discussed above.

While the invention has been disclosed with respect to a limited number of embodiments, those skilled in the art, having the benefit of this disclosure, will appreciate numerous modifications and variations therefrom. For example, the configurations and techniques described herein can be applied to test and measure the insulation resistance of any type of assembly in which one or more conductors are contained within a conductive sheath that is filled with an electrically insulative material. It is intended that the appended claims cover such modifications and variations as fall within the true spirit and scope of the invention.

What is claimed is:

1. A temperature sensing assembly for measuring temperature, comprising:
   a conductive sheath having an interior space;
   a conductor pair extending within the interior space of the conductive sheath, the conductor pair having a junction point electrically connected to the conductive sheath, the junction point being for measuring a temperature at a first location along the conductive sheath;
   a test electrical conductor extending within the interior space of the conductive sheath;
   an electrically insulative material disposed within the interior space of the conductive sheath to electrically isolate the test electrical conductor from the conductive sheath; and
   a terminal box having a first terminal electrically connected to a first conductor of the conductor pair, a second terminal electrically connected to a second conductor of the conductor pair, a third terminal electrically connected to the test electrical conductor, and a fourth terminal electrically connected to the sheath, wherein an electrical measurement between the first and second terminals provides an indication of the temperature at the first location and an electrical measurement between the third and fourth terminals provides an indication of insulation resistance of the temperature sensing assembly.

2. The assembly as recited in claim 1, wherein the conductor pair comprises a first conductor and a second conductor made of dissimilar materials.

3. The assembly as recited in claim 1, wherein the conductive sheath includes an end cap at a terminal end of the conductive sheath, and wherein the first location is at the end cap.

4. The assembly as recited in claim 1, wherein the terminal box is coupled to the conductive sheath.

5. The assembly as recited in claim 1, wherein the insulative material is made of one of magnesium oxide or alumina oxide.

6. The assembly as recited in claim 1, wherein the conductive sheath is made of one of Inconel, stainless steel or a nickel alloy.

* * * * *